US00PP13741P39

(12) United States Plant Patent
Kos

(10) Patent No.: US PP13,741 P3
(45) Date of Patent: Apr. 29, 2003

(54) LILY PLANT NAMED 'FUTURA'

(75) Inventor: Pieter Jan Kos, Anna Paulowna (NL)

(73) Assignee: World Breeding, B.V. (NL)

( * ) Notice: Subject to any disclaimer, the term of this patent is extended or adjusted under 35 U.S.C. 154(b) by 0 days.

(21) Appl. No.: 09/834,748

(22) Filed: Apr. 13, 2001

(65) Prior Publication Data

US 2002/0152528 P1 Oct. 17, 2002

(30) Foreign Application Priority Data

Apr. 14, 2000 (NL) ..... 2000/0595

(51) Int. Cl.[7] ..... A01H 5/00

(52) U.S. Cl. ..... Plt./313

(58) Field of Search ..... Plt./313

(56) References Cited

PUBLICATIONS

The New Royal Horticultural Society Dictionary of Gardening, vol. 3, editor–in–chief Anthony Huxley, The Royal Horticultural Society, 1992, pp. 68–80.*

* cited by examiner

*Primary Examiner*—Bruce R. Campell
*Assistant Examiner*—Anne Marie Grünberg
(74) *Attorney, Agent, or Firm*—Klarquist Sparkman LLP

(57) ABSTRACT

A new and distinct variety of upright Oriental×Aurelia hybrid lily plant, named 'Futura', characterized by large, yellow flowers.

1 Drawing Sheet

LATIN NAME OF THE GENUS AND SPECIES OF THE PLANT CLAIMED

Genus: Lilium. Species is unknown.

VARIETY DENOMINATION

'Futura'.

BACKGROUND OF THE INVENTION

The present invention relates to a new and distinct variety of Lilium hybrid referred to commercially as an upright Oriental×Aurelia lily hybrid and given the cultivar name 'Futura'.

This new variety is the product of a controlled breeding program using embryo culture and was carried out in the municipality of Breezand, The Netherlands, using the proprietary Oriental type hybrid lily E-890-19 as seed parent and the proprietary Aurelia type hybrid lily OR-90.058-8 as the pollen parent. The resulting plants were evaluated for cut flower production. Compared to the typical characteristics of common Oriental or Aurelia lily hybrids, this new variety has larger flowers, taller overall plant height and taller stems, and blooms earlier.

This new variety has not been observed under all possible environmental conditions. The phenotype may vary significantly with variations in environment such as temperature, light intensity, day length, and nutrient availability, without, however, any variations in genotype.

BRIEF SUMMARY OF THE INVENTION

The following traits have been repeatedly observed and are determined to be the basic characteristics of this invention that in combination distinguish this lily as a new and distinct variety:

1. floriferous habit;
2. large yellow flowers;

3. vigorous growth habit;
4. tall plant;
5. good virus tolerance; and
6. excellent vase-life.

Bulbs of this plant may be pre-cooled and forced out of season for very uniform cut flower production.

The primary distinguishing feature of 'Futura' is its numerous, large, yellow flowers. The seed parent, an Oriental type hybrid, does not produce yellow flowers, and 'Futura' can be bred approximately 25 days more quickly than the seed parent. The pollen parent, an Aurelian type hybrid, has a different inflorescence and calyx-like flowers. Furthermore, the flowers of the 'Futura' variety are larger than those produced by the pollen parent.

BRIEF DESCRIPTION OF THE DRAWING

This new variety of lily plant is illustrated in the accompanying photographic drawing, which shows the upper half portion of the flowering stem of a potted plant in the full face view of the flowers together with some foliage. The accompanying photograph, showing the 'Futura' variety, was taken in a studio and illustrates the typical flower and foliage form, with color as true as reasonably possible in this type of color illustration.

DETAILED BOTANICAL DESCRIPTION

This detailed description of the invention is based on plants approximately 80–90 days old produced in greenhouses in Breezand, The Netherlands. Bulbs were planted in (and the resulting plants cultivated in) trays with peatmoss. Plants were grown at a minimum temperature of about 15° C. without supplemental fertilization or supplemental lighting. Color references are provided according to The R.H.S. Colour Chart published by The Royal Horticultural Society of London, England, except where the context indicates a term having its ordinary dictionary meaning.

Origin: Resulting from a hybridization.

Parentage:

*Seed parent.*—Oriental type hybrid lily E-890-19 (proprietary owned).

*Pollen parent.*—Aurelia type hybrid lily OR 90.058-8 (proprietary owned).

Commercial classification: Upright Oriental×Aurelium hybrid lily, cut flower type.

Classification: Division VIII, all hybrids not provided for in any previous Division according to the Horticultural Classification of Lilies by The Royal Horticultural Society.

Form: Single erect stem from each bulb bearing terminal cluster of flowers.

Height: To about 140 cm. from the top of the soil to the top of the inflorescence.

Stem: Green in color (RHS 141B).

Growth: Vigorous, upright, and very strong. Plants grew about 120 cm over a span of about 80 to 90 days.

Foliage:

*Arrangement.*—Spiral.

*Quantity.*—Many fine leaves, with approximately 40 to 45 leaves per plant.

*Leaf size.*—To about 18.5 cm. long and to about 3 cm. wide.

*Leaf shape.*—Lanceolate.

*Leaf margin.*—Entire.

*Aspect.*—Glossy.

*Texture.*—Leathery.

*Color.*—Upperside of leaves: Green (RHS 137A). Underside of leaves: Green (RHS 139C). Leaf venation: Yellow-green (RHS 145A).

Bulb:

*Type.*—Concentric.

*Size.*—About 5.5 to 6.0 cm in diameter and about 16 to 18 cm in circumference.

*Color.*—Yellow-white (RHS 158C) and greyed-purple (RHS 184D).

Bud:

*Size.*—To about 13.5 cm. long and to about 3.5 cm wide, just prior to opening.

*Shape.*—Lanceolate, with the apex commonly having three obtuse tips.

*Color.*—Very Light Yellow (RHS 12C) at first opening turning into a Yellow (RHS 14C) when unfurling, blushed with Orange (RHS 35C).

*Opening rate.*—The mature bud opens slowly in response to light.

Flower:

*Blooming habit.*—Annually, once and profusely.

*Days to bloom.*—Flowers approximately 80 to 90 days after greenhouse planting under typical flower forcing conditions at minimum temperature of 15° C.

*Outdoor blooming time.*—Bulbs planted in mid-March bloom about mid-June.

*Greenhouse blooming time.*—Bulbs can be planted year-round and forced to bloom approximately 80 to 90 after planting. Greenhouse bloom lasts about 12 to 15 days.

*Flower number.*—About 4 to 5 flowers per plant.

*Flower size.*—Very Large.

*Diameter.*—To about 23 cm.

*Depth.*—To about 7 cm.

*Borne.*—Cluster of about 3 to 5 flowers from bulbs of about 14 to 16 cm. in circumference.

*Shape.*—The flower is funnel shaped. After opening, the tepals recurve at the top.

*Tepalage.*—Number: 6. Arrangement: Imbricated. Shape: Oval. Texture: Leathery. Aspect: Satiny. Size: Length: Inner tepals to about 13.6 cm. Outer tepals to about 14.5 cm. Width: Inner tepals to about 6.6 cm. Outer tepals to about 4 cm. Nectary: Green (RHS 145B), about 4.5 cm along vein. Spots: Orange-brown (RHS 171B) covering bottom one-third of tepal to halfway down nectary. Blush: None. Color, adaxial surfaces: Outer tepals are Yellow (RHS 12D) with midrib Yellow (RHS 4D). The inner tepals are Yellow (RHS 12C) with midrib Yellow (RHS 4D). Color, abaxial surfaces: Yellow-orange (RHS 14C) on the outer edge portion and yellow-orange (RHS 17B) toward the midrib. Some greyed-orange (RHS 170D) spots. Yellow-green (RHS 151B) keel. Fragrance: Weak.

*Lasting quality.*—Excellent. Each flower lasts about 14 days, with a vase life of about 12 to 15 days. Orientation: Ascending upwardly off the stem, the first flower to about a 40 degree angle, the last flower to about 90 degrees (horizontal).

*Pedicel.*—Length: About 8 to 9.5 cm. Color: Green (RHS 139C).

Reproductive organs:

*Stamens.*—Number: Six, typical of the genus Lilium.

*Anthers before dehiscense.*—Length: To about 4.2 cm. from mature bud. Color: Orange-brown (RHS 166A).

*Filaments.*—Length: To about 8.9 cm. Color: Yellow-green (RHS 145C).

*Pollen.*—Color: Orange (RHS 168B).

*Pistil.*—Number: One.

*Style.*—Length: To about 8.3 cm. Color: Green (RHS 145C) on top half, bottom half Lighter Green (RHS 145C).

*Stigma.*—Color: Dark Brown (RHS 200A).

Fruit:

*Fertility.*—Fruit is produced.

*Shape.*—Ovoid.

Fungal resistance: Some resistance to Pytium species. Color at maturity: Green (RHS 144B).

I claim:

1. A new and distinctive variety of Oriental×Aurelia hybrid lily plant, substantially as herein illustrated and described.

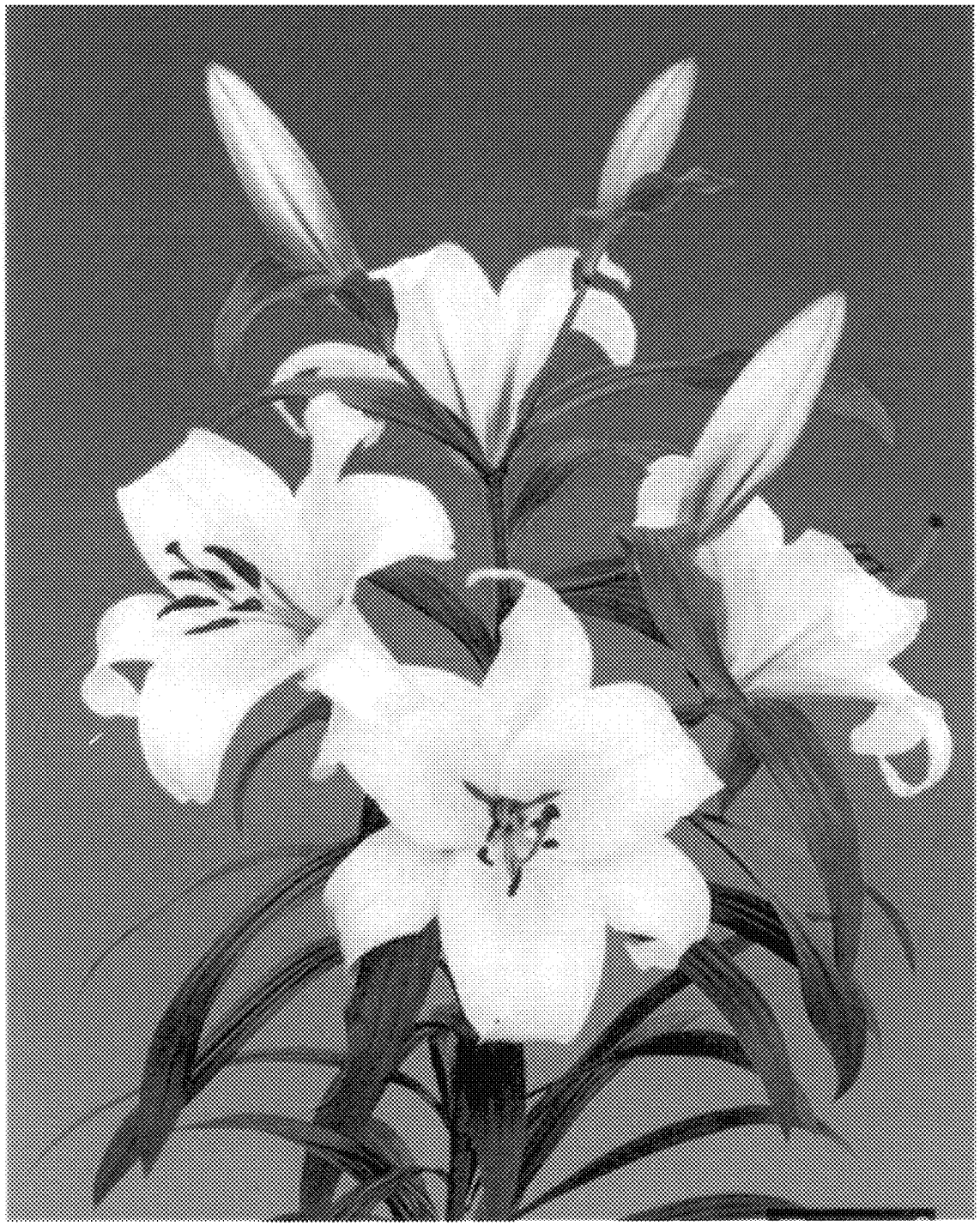

* * * * *